United States Patent [19]

Holtermann et al.

[11] Patent Number: 4,834,730

[45] Date of Patent: May 30, 1989

[54] CLOSURE CLAMP FOR BODY WASTE COLLECTING BAG

[75] Inventors: Henri Holtermann, Saint-Jean-De-Luz; Claude Hamelin, Ascain, both of France

[73] Assignee: Laboratories Biotrol, Paris Cedex, France

[21] Appl. No.: 148,613

[22] Filed: Jan. 26, 1988

[30] Foreign Application Priority Data

Jan. 30, 1987 [FR] France ............... 87 01119

[51] Int. Cl.$^4$ ............................................. A61F 5/44
[52] U.S. Cl. ............................ 604/335; 24/30.5 P; 24/543; 24/559; 128/346
[58] Field of Search ............... 128/346; 604/335, 332; 24/30.5 R, 30.5 P, 559, 562, 518, 487, 520, 543, 198, 199, 17 AP, 115 L, 132 WL

[56] References Cited

U.S. PATENT DOCUMENTS

| | | | |
|---|---|---|---|
| 2,818,871 | 1/1958 | Beaudry | 24/30.5 P |
| 3,385,298 | 5/1968 | Fenton | 604/339 |
| 3,503,397 | 3/1970 | Fogarty et al. | 128/346 |
| 3,523,534 | 8/1970 | Nolan | 604/335 |
| 3,874,042 | 4/1975 | Eddleman et al. | 128/346 |
| 4,296,529 | 10/1981 | Brown . | |
| 4,534,089 | 8/1985 | Swan | 24/559 |
| 4,551,888 | 11/1985 | Beecher | 128/346 |

FOREIGN PATENT DOCUMENTS

| | | | |
|---|---|---|---|
| 0620957 | 8/1962 | Belgium | 24/559 |
| 2932652 | 2/1981 | Fed. Rep. of Germany | 128/346 |
| 0091322 | 3/1958 | Norway | 24/487 |
| 2076881 | 12/1981 | United Kingdom . | |

Primary Examiner—C. Fred Rosenbaum
Assistant Examiner—Mario Costantino
Attorney, Agent, or Firm—Berman, Aisenberg & Platt

[57] ABSTRACT

An improved clamp is provided for closing a body waste collecting bag, molded from a plastic material piece and comprising two two legs hinged together about a film hinge, said legs being formed so as to clamp therebetween, in the operating condition, the films or sheets forming the collecting bag on the free emptying edge thereof, with removable means for immobilizing the legs with respect to each other, said legs with substantially rectangular flat contour being formed as the male and female parts of a resilient grip engagement coupling, said leg formed as the female part has a cross section somewhat in the form of a C with resiliently deformable wings, the leg formed as the male part has a partially conjugate cross section, and said legs defining simultaneously, at their end opposite the hinge end, a safety means also being of resilient grip type.

2 Claims, 1 Drawing Sheet

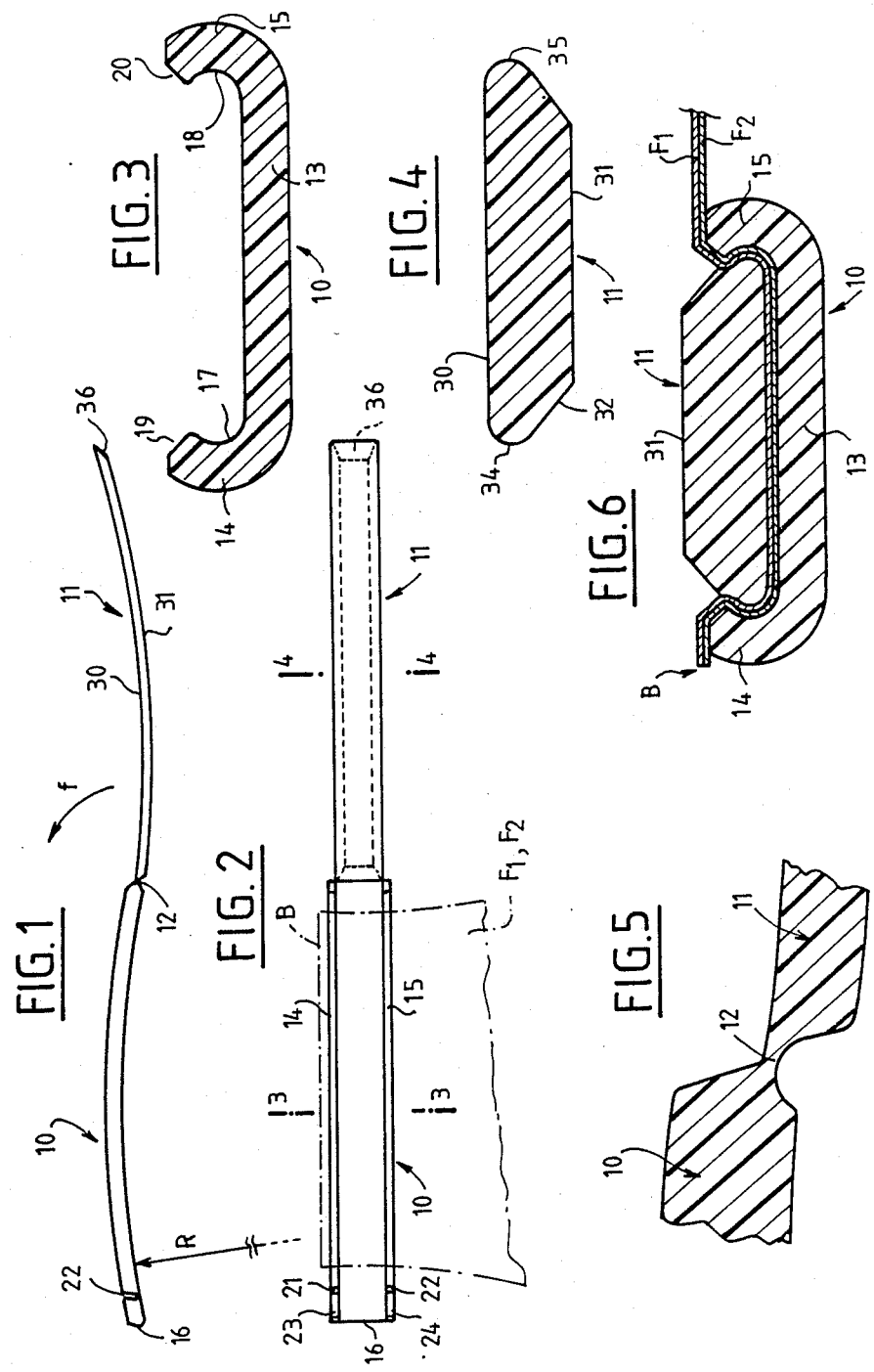

CLOSURE CLAMP FOR BODY WASTE COLLECTING BAG

BACKGROUND OF THE INVENTION

1. Field of the Invention

The invention relates to an improved clamp for closing body waste collecting bags of the type used by individuals having undergone surgical operations such as ileostomies or similar.

Such collecting bags, formed by a bag made from a plastic material film or sheet and having in one of their faces an opening adapted for connecting to the ostomy opening of the abdominal wall of a patient, are either of the "disposable" kind or of the "emptying" kind. For these latter, which are used particularly during post operative care, or by persons having undergone an ileostomy, a removable clamp is associated with each bag for sealingly closing the sheet or sheets forming the bag, at one end thereof distant from that collecting the body waste thus providing a closure which may be removed by a nurse or the patient himself for emptying the bag without it being necessary to separate it from the abdominal wall where it is fixed or held.

2. Description of the Prior Art

Numerous constructions of such clamps are known, for example from GB-A-2 976 881 or U.S. Pat. No. 3,523,534. The device disclosed in this latter document is of the "guillotine" type, that is to say is formed by two parallel walls of a body between which a blade may penetrate, by pivoting about a hinge, about which the edges of the opening of the collecting bag are folded, the dimensions of the blade, of the body and of the sheets being chosen so that the bag is sealingly closed by clampingly nipping its edges when the blade is entirely housed inside said walls. Snap fitting of the blade on the body, at the end opposite the pivoting end, prevents any untimely opening. Such a clamp is not easy to operate, in particular on opening, since, in order to remove the waste or excrements from the bag, the end thereof must be unfolded, after removing the blade, which may be a source of considerable discomfort.

Furthermore, such a device is only slightly deformable or not at all in its closed position in which it has three parallel parts, namely the two walls and the blade housed therebetween.

A construction of a different type is also known, in which the clamp is formed by molding a plastic material in the form of two legs hinged together about a film hinge with, for holding the legs one against the other in the closed position, a clip assembly means provided at the end opposite the hinge part. Such a device, described for example in U.S. Pat. No. 4,551,888, provides for clamping the edges of the collecting bag between multiple ribs of the two legs whose structure, like that of the assembly means, is thus relatively complex.

The problem arises then of providing an improved clamp which is simultaneously very easy to use, completely reliable insofar as closing the body waste collecting bag which it is intended to equip unconcerned and which, may further be at least slightly deformable without any disadvantages in its closed condition, thus allowing a certain adaptation to the morphology of the user.

SUMMARY OF THE INVENTION

This problem is solved by the fact that, in the device molded from a plastic material part and having two legs hinged together about a film hinge, said legs being formed so as to clamp therebetween, in the operating condition, the films or sheets forming the collecting bag on the free emptying edge thereof, with removable means for immobilizing the legs with respect to each other, said legs with substantially rectangular flat contour being formed as the male and female parts of a resilient grip engagement coupling, in accordance with the invention the leg formed as a female part has a cross section somewhat in the form of a C, whereas the leg formed as the male part has a partially conjugate cross section, said legs defining simultaneously, at their end opposite the hinge end, a safety means it also being of resilient grip type.

In a preferred embodiment, the safety means include a stirrup of a shape matching that of the male part, with slightly resilient wings, formed at the free end of the leg formed as the female part by cutting in the wings of the C two slits directed perpendicularly to said wings.

BRIEF DESCRIPTION OF THE DRAWINGS

The invention will be well understood from the following description, given by way of example, with reference to the accompanying drawings in which:

FIG. 1 is a side elevational view of an improved clamp of the invention;

FIG. 2 is a top view;

FIG. 3 is a sectional view through line III—III of FIG. 2 but on an appreciably larger scale. FIG. 4 is a sectional view through line IV—IV of FIG. 2 and on the same scale as that of FIG. 3;

FIG. 5 is a view on an even larger scale of the hinge zone of the two legs of the clamp; and FIG. 6 is an enlarged sectional view illustrating the operating condition for closing the collecting bag.

DESCRIPTION OF THE PREFERRED EMBODIMENTS

A clamp of the invention, for removably closing a body waste collecting bag, for example a bag which may be emptied of the type used by patients having undergone operations such as ileostomies, is molded from a piece of plastic material, for example a high density polyethylene copolymer such as that sold under the name "LACQTENE HD" by the firm ATOCHEM (Paris). As clearly shown in FIGS. 1 and 2, the clamp includes two legs 10 and 11 joined together by a film hinge 12, FIG. 5, each of the legs being molded to a substantially rectangular flat contour with, as clearly shown in FIG. 1, a profile with a large radius of curvature, illustrated schematically by R in FIG. 1. Legs 10 and 11 are further adapted so that the first one forms a female part and the second a male part with cross sections of partially mating shapes. More precisely, leg 10 or the female part has a C cross section, FIG. 3, with a web 13 and wings 14 and 15 which extend over practically the whole of the length of leg 10, from the free end 16 thereof to the hinge 12. Wings 14 and 15 are joined to web 13 by bends 17 and 18, respectively, and are each shaped, beyond said bends and inwardly of the piece, in the form of cut faces 19 and 20.

Wings 14 and 15 extend over practically the whole of the length of leg 10, except for two slits 21 and 22 formed close to end 16 and directed substantially perpendicularly to the large size longitudinal edges of said leg, formed by wings 14 and 15. These slits 21 and 22 thus define, at the free end of the female part - that is to say remote from the hinge 12 - a U shaped stirrup piece whose wings 23 and 24 are separate, from the mechanical point of view, from wings 14 and 15 of leg 10.

With this latter, leg 11 is adapted for cooperating whose cross section, FIG. 4, is of a substantially trapezoidal shape with a large base defining a face 30 and a small base defining a face 31, said faces being joined together by cut faces 32 and 33 contiguous with face 31 and rounded portions 34 and 35 respectively contiguous with face 30 and of the same radius as bends 17 and 18. At its free end, that is to say opposite hinge 12, leg 11 whose developed length is slightly greater than that of leg 10 has a flat 36 on its face 31.

The choice of the material forming the clamp, as well as the shapes and dimensions of the legs thereof, are such that leg 11 may be snap fitted into leg 10 when, by pivoting leg 11 about hinge 12 in the direction shown by arrow F in FIG. 1, said leg is brought first of all into contact with wings 14 and 15 of leg 10 then this movement is continued so as to urge said wings apart, by cooperation of the rounded portions such as 34 and 35 with the cut faces 19 and 20. At the end of the pivoting movement, the free end of leg 11 snap fits into the stirrup piece formed by wings 23 and 24 of the free end of leg 10, the portion of leg 11 corresponding to flap 36 then projecting slightly beyond the free edge of leg 10.

When, prior to closing the clamp as described immediately above, the two sheets or films $F_1$, $F_2$, FIG. 6, of the connecting bag are placed on wing 10, in the portion of the free edge B thereof which defines the emptying orifice, the described operation causes said two sheets or films to be sealingly nipped between the female part 10 and the male part 11, that is to say the sealed closure of the body waste collecting bag.

Opening of the clamp is caused by a movement which is the reverse of that described above, by bearing on face 30 of leg 11, in the zone of flat 36 projecting from leg 10, so as to extract said zone from wings 23 and 24 then, progressively, the rest of leg 11 from leg 10. At the end of the pivotal opening movement, the two films or sheets $F_1$, $F_2$ of the free edge of the bag are released so that the bag may be emptied without it having to be removed from the ostomy opening of the user.

Thus, said bag may be emptied in the flat position, such a mode of operation being particularly advantageous when a collecting bag is used during post operative care, or following surgical operations such as ileostomies.

The clamp of the invention, of low weight and small thickness, is particularly well adapted for closing a collecting bag worn under clothing which, because of its configuration, exerts a certain pressure force on the bag and the clamp. In such a case, the structure of the improved clamp of the invention allows deformation of the clamp, because of its inherent flexibility, which deformation may be modifying the radius of curvature R, perfectly match the clamp to the morphology of the thigh, or the abdomen of the patient using the bag, modification of this radius of curvature causing a slight relative longitudinal movement of one leg with respect to the other, without it adversely affecting the sealing of the closure, which is provided over the whole length of the clamp.

Good results have been obtained with the device of the invention in which the radius of curvature R of the two legs 10, 11, of the clamp was about 200 mm, the developed length of leg 10 about 81mm and that of leg 11 about 86 mm. In such a clamp, the thickness of leg 11 was of the order of 2.2 mm and its width about 8 mm, the clamp device being used for closing collecting bags in which the thickness of the constituent film, in the zone in the free edges, was of the order of 60 to 80 $\mu$m for each of the films, that is to say a thickness to be clamped by nipping of about 120 to 160 $\mu$m.

What is claimed is:

1. An improved clamp for closing a body waste collecting bag molded from a single piece of plastic material comprising first and second longitudinally curved legs connected to one another by an integrally formed plastic film hinge, said first and second legs having substantially the same radii of curvature, said first leg having along its whole length a substantially constant C-shaped cross section comprising resiliently deformable wings, said second leg having along its length a substantially constant cross section of conjugate shape with respect to said C-shaped cross section of the first leg so as to engage within said first leg to form a male-female coupling engagement, whereby said first and second legs seal the open end of said body waste collecting bag substantially over the whole inner surface area of said C-shaped leg, said first and second legs having respective free distal end portions with respect to said hinge defining a safety resilient gripping means for securely clamping said first and second legs together, and wherein said safety gripping means comprises the free end of said second leg which cooperates with slits in end portions of said wings of said C-shaped leg in the vicinity of the free end of said first leg for defining a U-shaped stirrup adapted to snappingly engage said free end of said second leg and hold said first and second legs in a closed condition of the clamp.

2. An improved clamp for closing a body waste collecting bag, said clamp being molded from a single piece of plastic material comprising:
a first longitudinally curved leg having a substantially constant C-shaped cross-section along its length, said C-shaped leg including resilient deformable wing portions,
a second longitudinally curved leg having substantially the same radius of curvature as the first leg, and having a substantially trapezoidal cross-section adapted for cooperatively mating within the C-shaped cross-section of the first leg, along the length of said first and second legs, wherein a wide base of the trapezoidal second leg is held within the resilient wing portions of the first leg, and
a plastic hinge integrally formed with said first and second legs connecting a first end of each of said legs to one another,
whereby the first and second legs clamp together to seal an open end of the body waste collecting bag therebetween, said bag being clamped between and following the contour of the C-shaped first leg and the trapezoidal second leg matingly engaged therewith,
wherein said first and second legs each further comprise second ends distant from said hinge, second end portions defining safety resilient gripping means comprising
a pair of slits spaced from the second end of the first leg, one cut in each of the wing portions of the C-shaped leg, perpendicularly to the length of the leg, forming a U-shaped stirrup adjacent said second end of said first leg, and
a free end of said second end portion of the second leg adapted for snappingly engaging said stirrup in a closed condition of the clamp,
whereby said clamp is opened by first opening said safety gripping means followed by disengaging the remainder of the clamped together legs.

* * * * *